(12) United States Patent
Hayes et al.

(10) Patent No.: US 7,041,857 B1
(45) Date of Patent: May 9, 2006

(54) HYDROGENATION OF ACETONE

(75) Inventors: Kathryn Sue Hayes, Plymouth Meeting, PA (US); John William Mitchell, Allentown, PA (US); Anita Niak, Germantown, MD (US); Michael Gerard Turcotte, Bethlehem, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/221,066

(22) Filed: Sep. 7, 2005

(51) Int. Cl.
C07C 29/145 (2006.01)
C07C 29/136 (2006.01)

(52) U.S. Cl. .................. 568/881; 568/876; 568/878; 568/880

(58) Field of Classification Search ............. 568/881, 568/876, 878, 880
See application file for complete search history.

(56) References Cited

U.S. PATENT DOCUMENTS

| | | |
|---|---|---|
| 2,614,107 A | 10/1952 | Wender et al. |
| 4,182,721 A | 1/1980 | De Thomas et al. |
| 5,081,321 A | 1/1992 | Fukuhara et al. |
| 5,449,838 A | 9/1995 | Knifton et al. |
| 5,495,055 A | 2/1996 | Rueter |
| 5,684,215 A | 11/1997 | Horn et al. |
| 5,866,725 A | 2/1999 | Unruh et al. |

FOREIGN PATENT DOCUMENTS

| | | |
|---|---|---|
| JP | 62012729 | 1/1987 |
| JP | 03133941 | 6/1991 |
| JP | 03141235 | 6/1991 |

*Primary Examiner*—Elvis O. Price
(74) *Attorney, Agent, or Firm*—Mary E. Bongiorno; Russell R. Brewer

(57) ABSTRACT

This invention relates to an improvement in a liquid phase process for producing isopropanol by the hydrogenation of acetone in the presence of a hydrogenation catalyst; the improvement comprising;
 contacting acetone with hydrogen under continuous liquid phase conditions; and,
 employing a sponge metal catalyst promoted with an effective amount of chromium.

11 Claims, No Drawings

HYDROGENATION OF ACETONE

BACKGROUND OF THE INVENTION

Isopropanol has industrial use in the manufacture of a wide variety of chemicals including isopropyl amine and various ethers. One of the industrial processes for producing isopropanol is by the hydrogenation of acetone. In these processes an acetone containing feedstock is contacted with hydrogen in the presence of a hydrogenation catalyst to produce a crude product.

It has become an objective in some of the processes to employ the reaction product from the hydrogenation of acetone without purification for the synthesis of industrial chemicals. In the manufacture of isopropyl amine by the amination of isopropanol, it is necessary to convert substantially all of the acetone in the hydrogenation reaction product in order to prevent amine contamination. Achieving high conversion of acetone to isopropanol and excellent reaction rates have been objectives of these processes.

The following patents are representative of processes for the hydrogenation of carbonyl compounds including acetone:

U.S. Pat. No. 5,081,321 discloses a process for the catalytic hydrogenation of acetone by feeding hydrogen and acetone in liquid phase to a reactor having a fixed catalyst bed from its top to form a cocurrent gas/liquid flow and maintaining a trickle bed state. Raney nickel, e.g., Raney nickel alloy (Ni/Al) as well as copper based catalysts, e.g., copper-chromium; nickel based catalysts and the platinum group catalysts, e.g., palladium, ruthenium, rhodium and the like, are suggested as candidates.

U.S. Pat. No. 5,449,838 discloses a two step process for generating isopropyl-t-butyl ether wherein the first step resides in the vapor phase hydrogenation of acetone to isopropanol and the second step resides in the conversion of the isopropanol reaction product to isopropyl-t-butyl ether. In the first step crude acetone is passed over a bulk metal catalyst comprised of a nickel-rich catalyst characterized as having the composition, calculated in mol %, of from about 60%–85% nickel, 1%–30% copper and 0.1%–6% chromium with the preferred proportions being about 65%–78% nickel, 10%–20% copper and 1%–3% chromium.

U.S. Pat. No. 5,495,055 discloses a process for the fixed bed hydrogenation of acetone to isopropanol using a ruthenium based catalyst.

U.S. Pat. No. 4,182,721 discloses processes for the hydrogenation of carbonyl compounds using a Raney nickel catalyst having molybdenum adsorbed thereon. The patentees noted that conventional Raney nickel catalysts are not entirely satisfactory because of their relative inactivity.

JP 62-012729 A (abstract and translation of examples and claims) discloses a process for preparing isopropanol by the batch hydrogenation of acetone at a pH 7.0–8.2 over Raney nickel catalyst at 100–160° C. In one example, 300 ml of a mixture containing 66.4 wt % acetone, 33.3 wt % isopropanol, and 0.3 wt % water is hydrogenated over 15.7 g Raney nickel at 150° C., 370 psig, and pH 7.6 for 30 minutes to give 99.3% conversion of acetone and 100% selectivity to isopropanol (IPOH).

U.S. Pat. No. 5,684,215 discloses a process for the preparation of an alcohol by reacting a carbonyl compound, e.g., a ketone or aldehyde, with hydrogen over a supported catalyst containing nickel, aluminum and zirconium at temperatures of from 60 to 150° C. Both liquid phase and gas phase reactions are described.

U.S. Pat. No. 2,614,107 discloses a process for the reduction of carbonyl compounds such as aldehydes and ketones using synthesis gas as the reducing agent. Example 5 shows the hydrogenation of acetone to isopropanol under liquid phase conditions using a cobalt acetate catalyst. Other catalysts suggested as being suited for hydrogenation include iron, nickel, ruthenium, rhodium, platinum and palladium.

JP 03-141235 A (JP 2834495 B2) (machine translation) discloses a process for hydrogenation of acetone in which isopropanol is circulated at 800 ml/h and 100° C. to a reactor having a fixed layer of Raney nickel catalyst. Acetone at 79 g/h and hydrogen at 66.6 L/h are continuously fed to the reactor. The reactor pressure is 20 kgf/cm$^2$, and the reactor temperature is 106.8° C. Acetone conversion is 99.8%, and isopropanol selectivity is 99.9% vs. 70.5% acetone conversion and 92.2% isopropanol selectivity when the hydrogenation is conducted without circulation of the reaction mixture.

JP 03-133941 A (JP 2786272 B2) (machine translation) discloses the hydrogenation of acetone in a fixed bed using a Raney nickel catalyst. Isopropanol is produced in 99.9% yield with 99.9% conversion of acetone.

BRIEF SUMMARY OF THE INVENTION

This invention relates to an improvement in a process for producing isopropanol by the hydrogenation of acetone in the presence of a hydrogenation catalyst. The improvement comprises:
  contacting acetone with hydrogen under liquid phase conditions; and,
  employing a hydrogenation catalyst comprising a sponge or Raney metal catalyst promoted with an effective amount of chromium.

Significant advantages in terms of improving the hydrogenation of acetone have been achieved and these include:
  an ability to produce isopropanol by a continuous liquid phase process and achieve excellent reaction rates; and,
  an ability to achieve excellent conversion of acetone to isopropanol and allowing for use of the crude hydrogenation product as a feedstock for the production of isopropylamines by amination.

DETAILED DESCRIPTION OF THE INVENTION

In the production of amines by the amination of an isopropanol feedstock obtained by the hydrogenation of acetone, it is desired the isopropanol feedstock contain less than 5%, preferably less than 2%, by weight unreacted acetone. If acetone concentrations are greater than 5%, the reaction product, in many cases, has to be purified prior to use. Otherwise, the contaminating acetone in the feedstock, e.g., as in amination reactions for the production of isopropylamine, may contribute to catalyst deactivation, poor reaction rates, excessive byproduct formation and contamination of product.

In the improved process for producing isopropanol, acetone is hydrogenated under continuous liquid phase conditions. Liquid phase hydrogenation of acetone in stirred tank reactors using Raney metal catalysts has been employed but these processes often suffer from poor catalyst productivity, where catalyst productivity is defined as the grams acetone converted per cc catalyst per hour. It has been found that when the liquid phase hydrogenation process is carried out employing sponge or Raney metal catalysts containing chromium as a promoter, one unexpectedly finds greater catalyst productivity or activity. Under high mass transfer conditions, the reaction can be conducted at low pressure, e.g., 100 to 2000 psig (791 to 13,891 kPa), preferably from 150 to 1500 psig (1136 to 10,444 kPa), and moderate temperatures, e.g., 60 to 200° C., preferably 80 to 160° C., to achieve excellent rate and conversion. By implementing these process conditions, high catalyst productivity can be achieved.

The sponge metal or Raney metal catalysts employed in the reaction contain from 0.1 to 10%, preferably about 0.5 to 3%, by weight chromium based upon the weight of the catalyst, as a promoter. Sponge nickel promoted with chromium is the preferred catalyst, although sponge cobalt or Raney cobalt is well suited. These catalysts are employed in the reaction medium in an amount conventionally used in liquid phase hydrogenation reactions. Typically, the amount of catalyst supplied to the reaction medium is from 0.5–20%, preferably from 1–10% by weight, of the initial liquid charge, e.g., isopropanol or acetone, to the reactor.

The terms sponge metal and Raney metal catalysts are intended to refer to nickel and cobalt catalysts having a skeletal structure formed from a nickel or cobalt alloy. Typically, these catalysts are formed from nickel or cobalt alloyed with aluminum and the aluminum subsequently removed. Included with the terms sponge nickel and sponge cobalt are the trademarked and well known Raney nickel and Raney cobalt catalysts.

Optionally, from 0.1 to 10% by weight of other components, e.g., iron (Fe) or molybdenum (Mo), may be included in the catalyst, but their presence is not required to achieve the improved catalyst productivity.

The reaction may be carried out using a carrier for the acetone feedstock. If a carrier is employed it is preferred that it is isopropanol because it becomes non-contaminating with the reaction product.

The following examples are provided to illustrate various embodiments of the invention.

General Procedure: Catalysts were obtained from either W. R. Grace or from Activated Metals, Inc. (Activated Metals, Inc. purchased by Johnson Matthey). Catalyst density was assumed to be 7 g/cc for all catalysts. Batch hydrogenation experiments were conducted in a 300 cc Autoclave Engineers reactor. Semi-batch and continuous hydrogenation reactions were run in a 1.8 L Mettler Toledo RC1 Calorimeter Reactor System. Acetone was pumped to the reactor via ISCO syringe pumps or a Lewa diaphragm pump. In Continuous Stirred Tank Reactor (CSTR) mode, a constant level in the reactor was maintained by a Kammer valve level controller in conjunction with a Drexel level probe which were operated via the RC1 system.

EXAMPLE 1

Batch Hydrogenation

A 300 cc autoclave was charged with 145.0 g acetone and 2.9 g catalyst. The reactor was sealed and purged three times with nitrogen then three times with hydrogen. The reactor was pressurized to 300 psig (2170 kPa) with hydrogen and heated to the desired temperature, typically 80° C. Hydrogen consumption was monitored from a 1 L ballast. The reaction was continued for 5–10 minutes after the hydrogen uptake stopped and then was cooled to room temperature and vented. The product was filtered and analyzed by GC. Catalyst screening results for the various runs are shown in Table 1 below.

TABLE 1

| Run | Catalyst | Catalyst Promoter | Reaction Time, min | Wt % Acetone Conversion |
|---|---|---|---|---|
| A | A4000 Sponge Nickel (chromium-promoted) | 2.5% Cr; 2% Fe | 22 | 99.99 |
| B | Raney Cobalt 2724 (chromium promoted) | 2.15% Cr, 0.3% Fe | 28 | 99.99 |
| C | A7000 Sponge Nickel (molybdenum promoted) | 2% Mo 0.4% Fe | 35 | 99.93 |
| D | A5000 Sponge Nickel | None 0.2% Fe | 45 | 99.92 |
| E | Raney Nickel 3300 (molybdenum promoted) | 1.1% Mo 0.2% Fe | 46 | 99.94 |
| F | Raney Nickel 4200 | None 0.5% Fe | 62 | 99.92 |

The results show that the sponge nickel and Raney cobalt catalysts promoted with chromium (Cr) afforded the best reaction times including that of showing greater activity than Raney nickel promoted with Mo and unpromoted Raney nickel. Excellent conversions, i.e., 99+% were achieved.

Although each catalyst incorporated some Fe, its effect on catalyst productivity, if any, was significantly less than Cr or Mo as a promoter. Molybdenum has been reported as a promoter for these catalysts and it was surprising to see that chromium was slightly superior at similar promoter levels (compare Examples B and C).

EXAMPLE 2

Semi-Batch Hydrogenation

The reactor was pressure checked and charged with 470 g of isopropanol and the specified quantity of catalyst. The reactor was purged with nitrogen and then with hydrogen at room temperature. The reactor was pressurized to 150 psig (1136 kPa) with hydrogen. The temperature was set to reach 120° C. in 20 minutes, and the stirrer speed was increased to 1000 rpm over 5 minutes. When the temperature reached 120° C., the reactor was pressurized to 300 psig (2170 kPa). The pump speed was set to the desired value, and flow of acetone to the reactor was initiated. After 30 minutes, the reactor was sampled. The sample was analyzed by GC to determine wt % acetone conversion. Catalyst types, levels, and acetone conversion data for the runs are shown in Table 2. Selectivity to isopropanol exceeded 99% for all catalysts.

TABLE 2

| Run | Catalyst | Promoter | Catalyst charge, g | Acetone Feed Rate, g/h | Wt % Acetone Conversion |
|---|---|---|---|---|---|
| A | Raney Cobalt 2700 | None | 7.8 | 600 | 82.5 |
| B | Raney Cobalt 2724 | 2.15% Cr, 0.3% Fe | 7.5 | 570 | 97.2 |
| C | Sponge Nickel A4000 | 2.5% Cr, 2% Fe | 7.7 | 600 | 99.5 |

The results show that both of the promoted Raney metal catalysts resulted in excellent conversion of acetone while the unpromoted Raney cobalt catalyst resulted in about 82% conversion. Because Example A shows a significantly low conversion, the reaction product would require purification before it was suited for use as an amine producing feedstock or, in the alternative, the acetone feed rate would have to be reduced to produce a feedstock suitable for use in many industrial processes. As in Example 1, the activity of the chromium promoted sponge nickel was superior to the unpromoted Raney cobalt.

EXAMPLE 3

Continuous Stirred Tank Reactor

Acetone was hydrogenated in a continuous stirred tank reactor as follows: Raney cobalt 2724 catalyst, 11.75 g (2.5 wt % based on the weight of isopropanol), was charged to the reactor along with 470 g of isopropanol. The reactor was heated to 120° C. and pressurized to 300 psig (2170 kPa) with hydrogen. Acetone was pumped to the reactor at a rate corresponding to a space-time of 0.65 hr. Samples were taken periodically for analysis. Acetone conversion was 99.2 wt %. Catalyst productivity was 431 g acetone converted per cc catalyst per hour.

EXAMPLE 4

Continuous Stirred Tank Reactor

Isopropanol, 470 g, and A4000 sponge nickel catalyst, 24.4 g (5.2 wt %), were charged to a stirred tank reactor. The reactor was heated to 120° C. and pressurized to 200 psig (1480 kPa) with hydrogen. Acetone was fed to the reactor at a rate corresponding to a space-time of 0.5 hr. Acetone conversion was measured to be 98.7 wt %. Catalyst productivity was 269 g acetone converted per cc catalyst per hour.

EXAMPLE 5

Continuous Stirred Tank Reactor

The procedure of Example 4 was repeated except that the A4000 sponge nickel catalyst charge was 2 wt %, the reaction temperature was increased to 140° C. and the reaction pressure was increased to 1000 psig (6996 kPa). Acetone conversion was 99.3%. Catalyst productivity was 532 g acetone converted per cc catalyst per hour.

Summarizing, Examples 3–5 demonstrate the continuous hydrogenation of acetone in the liquid phase to produce an isopropanol containing reaction product of high quality and suitable for use as a feedstock without further purification. Chromium-promoted Raney/sponge metal catalysts were demonstrated to have superior activity relative to unpromoted Raney or sponge cobalt catalysts or sponge metal catalysts containing other promoters. Sponge or Raney nickel promoted with chromium is shown as the preferred catalyst and shows the highest reactivity for this hydrogenation. Examples 4 and 5 show the effects of reaction pressure and temperature on the productivity of the chromium-promoted Raney nickel catalyst.

Catalyst productivities under continuous liquid phase hydrogenation conditions for nickel and cobalt catalysts promoted with chromium, as shown in Examples 3–5, were unexpectedly quite high, ranging from 269 to 532 g acetone converted per cc catalyst per hour. Liquid phase hydrogenation, in contrast to vapor phase hydrogenation, results in these exemplified catalysts being about four orders of magnitude higher than similar bulk metal catalysts employed in a vapor phase reaction such as the process described in Example 1 of U.S. Pat. No. 5,449,838. The catalyst productivities obtained in Examples 3–5 are 2–4 times higher when compared to the catalyst productivity described in the batch liquid phase reaction of JP 62-012729.

What is claimed is:

1. In a process for producing isopropanol by the hydrogenation of acetone in the presence of a hydrogenation catalyst; the improvement which comprises the steps:
    contacting acetone with hydrogen under continuous liquid phase conditions; and,
    employing a hydrogenation catalyst comprising a sponge metal catalyst promoted with an effective amount of chromium promoter.

2. The process of claim 1 wherein the chromium promoter is present in an amount of from 0.1 to 10% by weight of the sponge metal catalyst.

3. The process of claim 2 wherein hydrogenation is carried out at a pressure of from 100 to 2000 psig.

4. The process of claim 3 wherein hydrogenation is carried out at a temperature of from 60 to 200° C.

5. The process of claim 4 wherein the hydrogenation is carried out in the presence of isopropanol as a carrier.

6. The process of claim 2 wherein the sponge metal catalyst is sponge nickel.

7. The process of claim 6 wherein the chromium in the sponge nickel catalyst is present in an amount from 0.5 to 3% by weight of the total weight of the catalyst.

8. The process of claim 2 wherein the sponge metal catalyst is sponge cobalt.

9. The process of claim 8 wherein the chromium in the sponge cobalt catalyst is present in an amount from 0.5 to 3% by weight of the total weight of catalyst.

10. A process for the hydrogenation of acetone which comprises:
    (a) charging a mixture of isopropanol and a hydrogenation catalyst to a reactor, the catalyst being present in an amount from 0.1 to 10% by weight of the isopropanol;
    (b) employing a sponge nickel or sponge cobalt catalyst as said hydrogenation catalyst, the catalyst promoted with from 0.5 to 3% by weight chromium, based on the total weight of catalyst;
    (c) continuously charging acetone and hydrogen to the reactor under conditions for effecting hydrogenation of said acetone; and,
    (d) continuously removing isopropanol from the reactor consistent with the rate of isopropanol formation in the reactor.

11. The process of claim 10 wherein hydrogenation is carried out at a temperature of from 60 to 200° C. and a pressure of from 100 to 2000 psig.

* * * * *